United States Patent
Nett et al.

(10) Patent No.: US 9,619,889 B2
(45) Date of Patent: Apr. 11, 2017

(54) METHODS AND SYSTEMS FOR NORMALIZING CONTRAST ACROSS MULTIPLE ACQUISITIONS

(71) Applicant: General Electric Company, Schenectady, NY (US)

(72) Inventors: Brian Edward Nett, Brookfield, WI (US); Chuang Miao, Winston-Salem, NC (US)

(73) Assignee: General Electric Company, Schenectady, NY (US)

(*) Notice: Subject to any disclaimer, the term of this patent is extended or adjusted under 35 U.S.C. 154(b) by 350 days.

(21) Appl. No.: 14/520,190

(22) Filed: Oct. 21, 2014

(65) Prior Publication Data
US 2016/0110892 A1    Apr. 21, 2016

(51) Int. Cl.
| | | |
|---|---|---|
| *G06K 9/00* | (2006.01) | |
| *G06T 7/00* | (2017.01) | |
| *A61B 19/00* | (2006.01) | |
| *A61B 6/00* | (2006.01) | |
| *G06T 5/00* | (2006.01) | |

(52) U.S. Cl.
CPC ............ *G06T 7/0081* (2013.01); *A61B 6/481* (2013.01); *A61B 6/52* (2013.01); *A61B 6/5258* (2013.01); *A61B 19/5225* (2013.01); *G06T 5/008* (2013.01); *A61B 2019/5236* (2013.01); *A61B 2019/5242* (2013.01);
(Continued)

(58) Field of Classification Search
CPC ....... A61B 19/5225; A61B 6/481; A61B 6/52; A61B 6/5258; A61B 2019/5236; A61B 2019/5242; A61B 2019/5276; A61B 2576/00; G06T 5/008; G06T 7/0081; G06T 2207/10081
See application file for complete search history.

(56) References Cited

U.S. PATENT DOCUMENTS

| 5,848,117 A | 12/1998 | Urchuk et al. |
| 7,636,462 B2 * | 12/2009 | Li .......................... G06T 3/0056 |
| | | 128/922 |

(Continued)

FOREIGN PATENT DOCUMENTS

WO    2013/068887 A1    5/2013

OTHER PUBLICATIONS

Miao, C. et al., "Revolution Program: Multi-Slab Contrast Agent DC Correction," Jul. 14, 2013, pp. 1-46.*
(Continued)

*Primary Examiner* — Amara Abdi
(74) *Attorney, Agent, or Firm* — McCoy Russell LLP

(57) ABSTRACT

Various methods and systems are provided for correcting contrast banding artifacts across multiple acquisitions in reconstructed images. In one embodiment, a method for computed tomography imaging comprises generating an original image comprising multiple subvolumes, segmenting the original image into different structures for each subvolume, selectively applying a mask-based correction through each area of subvolume that includes continuous structures to generate an updated image, and performing streak correction between the original image and the updated image to generate a final image. In this way, image quality may be improved without adjusting anatomical structures in an image.

20 Claims, 11 Drawing Sheets

(52) U.S. Cl.
CPC ... *A61B 2019/5276* (2013.01); *A61B 2576/00* (2013.01); *G06T 2207/10081* (2013.01)

(56) References Cited

U.S. PATENT DOCUMENTS

| | | | |
|---|---|---|---|
| 2007/0127797 A1* | 6/2007 | Angelos | A61B 6/032 382/128 |
| 2010/0246922 A1* | 9/2010 | Uchihara | G06T 5/004 382/132 |
| 2011/0026791 A1* | 2/2011 | Collins | G06K 9/62 382/131 |
| 2012/0076379 A1* | 3/2012 | Dempsey | G06T 5/002 382/131 |
| 2012/0230576 A1* | 9/2012 | Rohler | A61B 6/032 382/132 |
| 2014/0072108 A1* | 3/2014 | Rohler | A61B 6/482 378/207 |
| 2014/0081132 A1* | 3/2014 | Dwivedi | G06T 7/0081 600/425 |
| 2014/0286558 A1* | 9/2014 | Koehler | G06T 5/005 382/131 |

OTHER PUBLICATIONS

International Search Report and Written Opinion from Corresponding PCT application No. PCT/US2015/050705 dated Dec. 2, 2015; 10 pages.

Miao, C. et al., "Revolution Program: Multi-Slab Contrast Agent DC Correction," Jul. 14, 2013, 46 pages.

* cited by examiner

METHODS AND SYSTEMS FOR NORMALIZING CONTRAST ACROSS MULTIPLE ACQUISITIONS

FIELD

Embodiments of the subject matter disclosed herein relate to non-invasive imaging, and more particularly, to correcting contrast banding artifacts produced during image reconstruction.

BACKGROUND

In computed tomography (CT) and fluoroscopy imaging systems, X-ray radiation spans a subject of interest, such as a human patient, and a portion of the radiation impacts a detector or a photographic plate where the image data is collected. In some X-ray systems, the photographic plate is then developed to produce an image, which may be used by a radiologist or attending physician for diagnostic purposes. In digital X-ray systems, a photodetector produces signals representative of the amount or intensity of radiation impacting discrete pixel regions of a detector surface. The signals may then be processed to generate an image that may be displayed for review. In CT systems, a detector array including a series of detector elements produces similar signals through various positions as a gantry is displaced around a patient.

In the images produced by such systems, contrast is created based upon the varying attenuation of the X-rays by the materials encountered as the X-rays penetrate the patient's tissue. Typically, materials having atoms with a greater atomic number will have a greater attenuation of X-rays. Thus, tissues such as bone may create relatively high contrast within an image compared to other tissues, such as fatty tissue. Some techniques used for CT and fluoroscopy imaging use a contrast agent to artificially create contrast within an area that would typically not have relatively high contrast, such as blood vessels. The contrast agents may include one or more atoms capable of attenuating X-rays with a relatively high degree of efficiency, such as iodine. For example, in CT angiography, a contrast agent is typically injected into the patient, followed by CT imaging. The contrast agent typically perfuses through certain tissues of the patient, and the resulting CT images contain regions of enhanced contrast corresponding to the areas that are perfused with the contrast agent.

The images produced by such systems may include data acquired at different times. As contrast agent takes time to perfuse, the contrast levels may differ during the time of each data acquisition. As a result, an image reconstructed from multiple acquisitions may include contrast banding artifacts. Such artifacts can lead to confusion for a physician and patient reviewing the final image.

BRIEF DESCRIPTION

In one embodiment, a method for computed tomography imaging comprises generating an original image comprising multiple subvolumes, segmenting the original image into different structures for each subvolume, selectively applying a mask-based correction through each area of subvolume that includes continuous structures to generate an updated image, and performing streak correction between the original image and the updated image to generate a final image. In this way, image quality may be improved without adjusting anatomical structures in an image.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

The following description relates to various embodiments of medical imaging systems. In particular, methods and systems are provided for correcting contrast banding artifacts across multiple acquisitions in reconstructed images. For example, correcting contrast banding artifacts may include adjusting the DC, or zero frequency, components of an image using a mask-based approach. An example of a computed tomography (CT) imaging system that may be used to acquire images processed in accordance with the present techniques is provided in FIGS. 1 and 2. Though a CT system is described by way of example, it should be understood that the present techniques may also be useful when applied to images acquired using other imaging modalities, such as tomosynthesis, MRI, PET, SPECT, C-arm angiography, mammography ultrasound, and so forth. The present discussion of a CT imaging modality is provided merely as an example of one suitable imaging modality.

Figure 1:
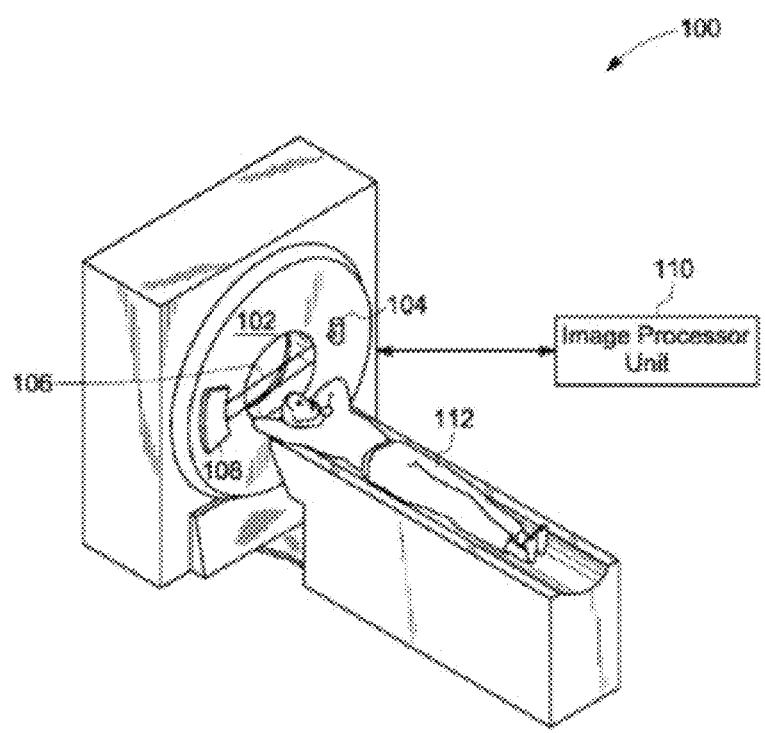
FIG. 1 is a diagrammatical view of a CT system according to an embodiment of the invention.
Figure 2:
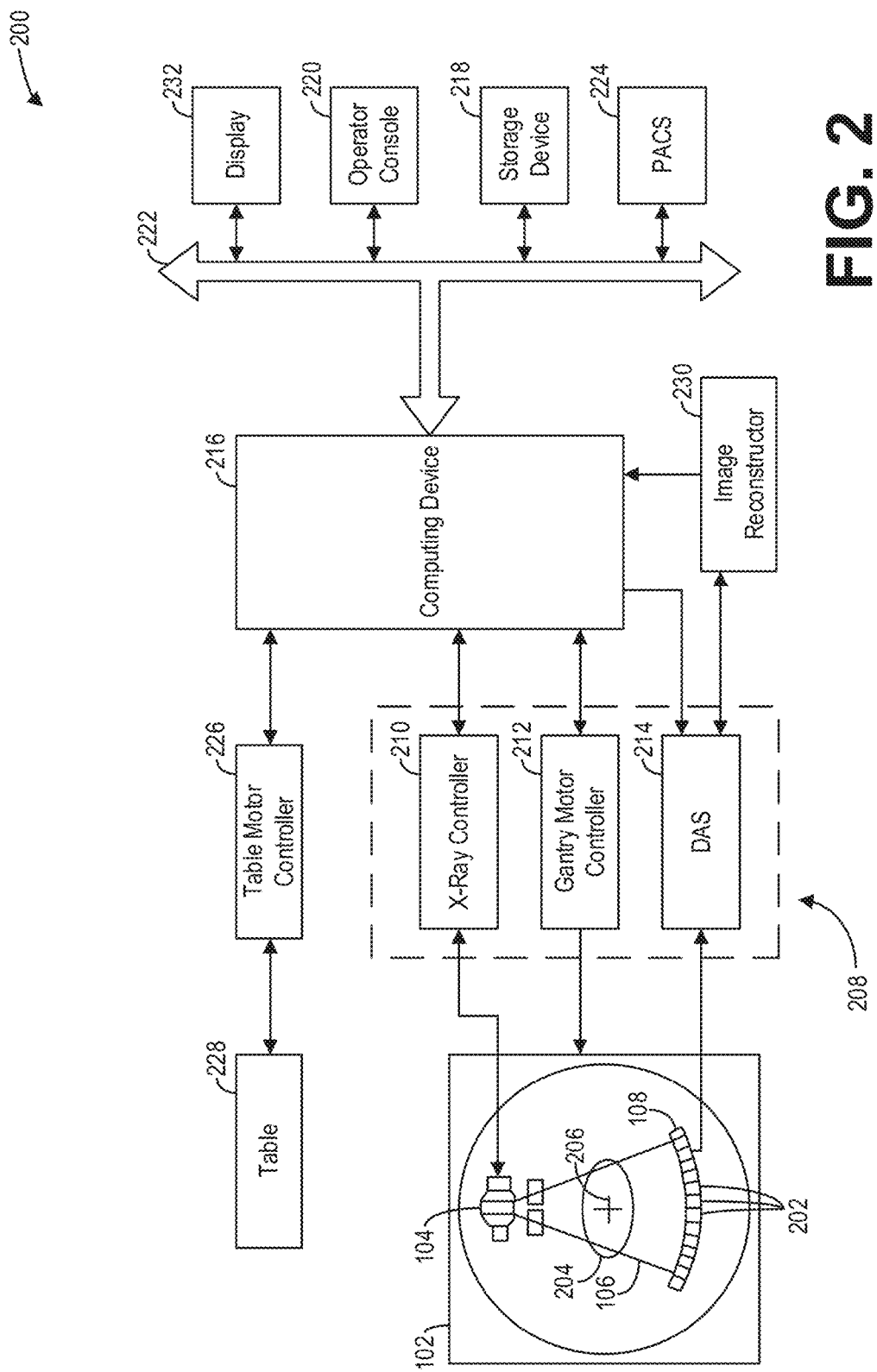
FIG. 2 is a block schematic diagram of an exemplary imaging system according to an embodiment of the invention.
Figure 3:
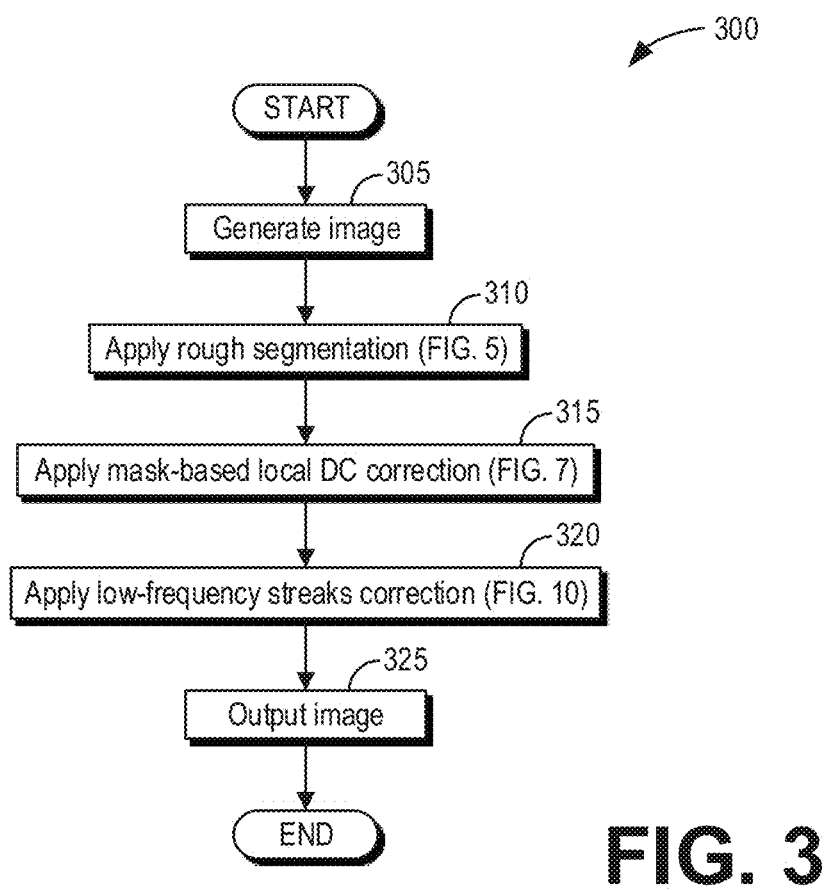
FIG. 3 shows a high-level flow chart illustrating an example method for multi-slab contrast agent DC correction according to an embodiment of the invention.
Figure 4:
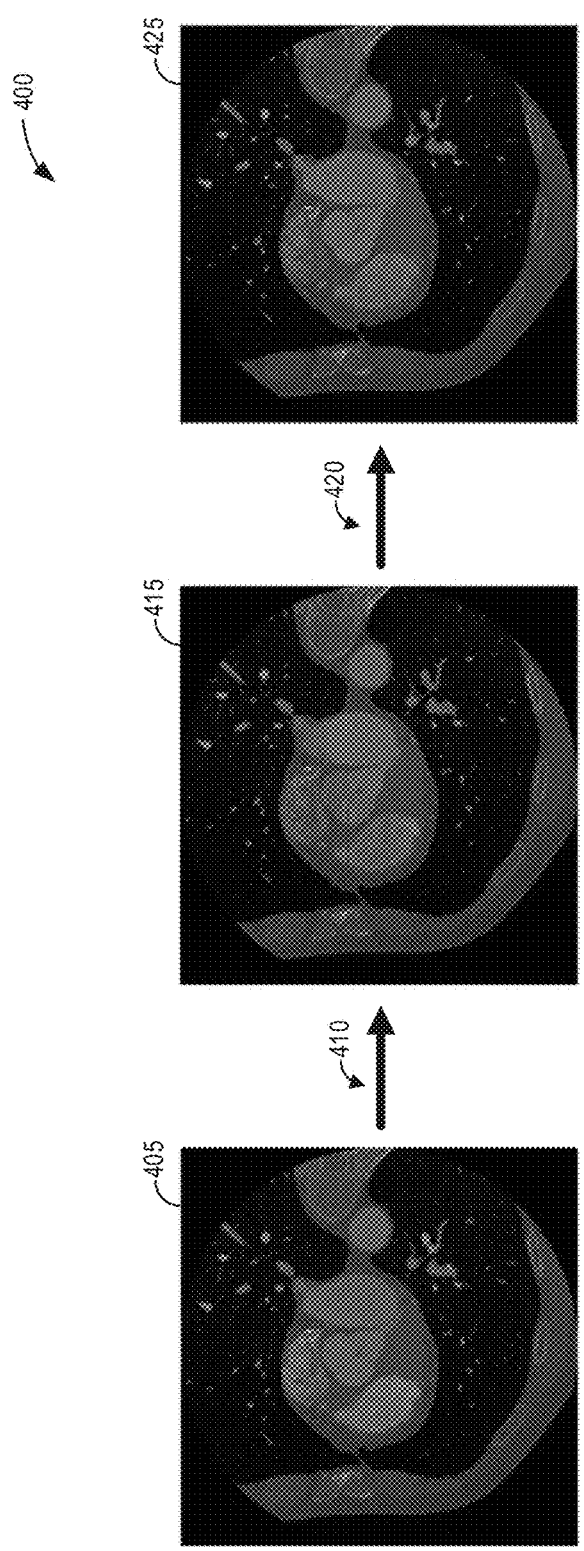
FIG. 4 shows a pictorial overview of multi-slab contrast agent DC correction according to an embodiment of the invention.
Figure 5:
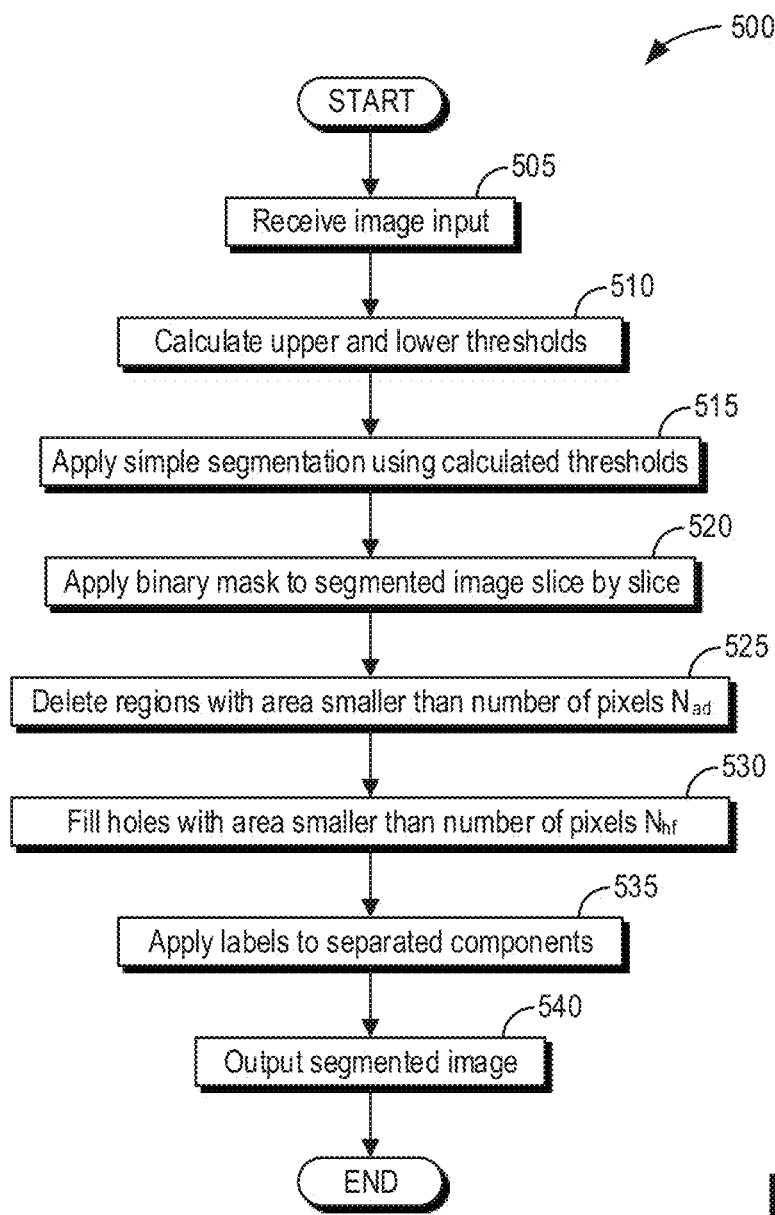
FIG. 5 shows a high-level flow chart illustrating an example method for applying rough segmentation according to an embodiment of the invention.
Figure 6:
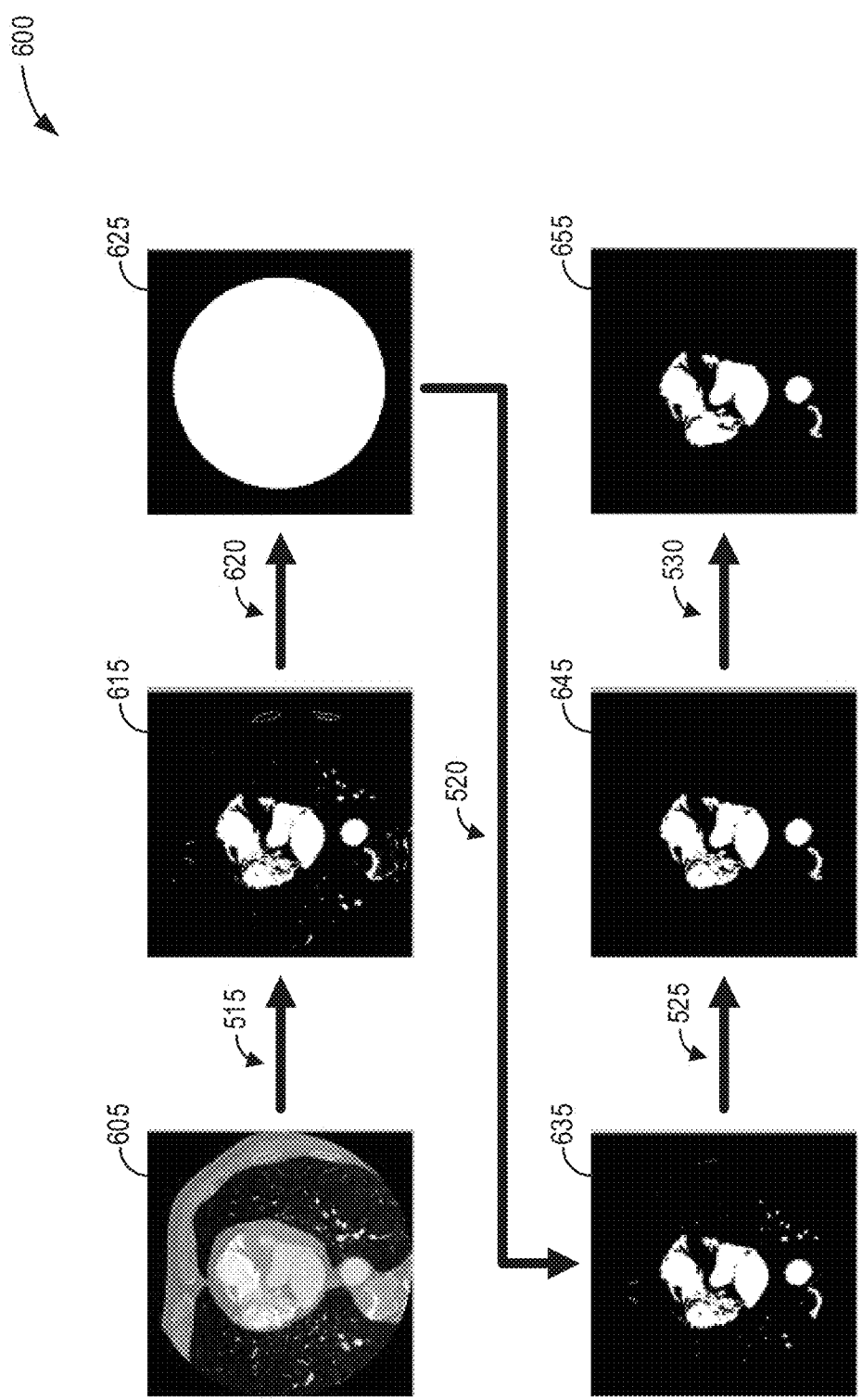
FIG. 6 shows a pictorial overview of rough segmentation according to an embodiment of the invention.
Figure 7:
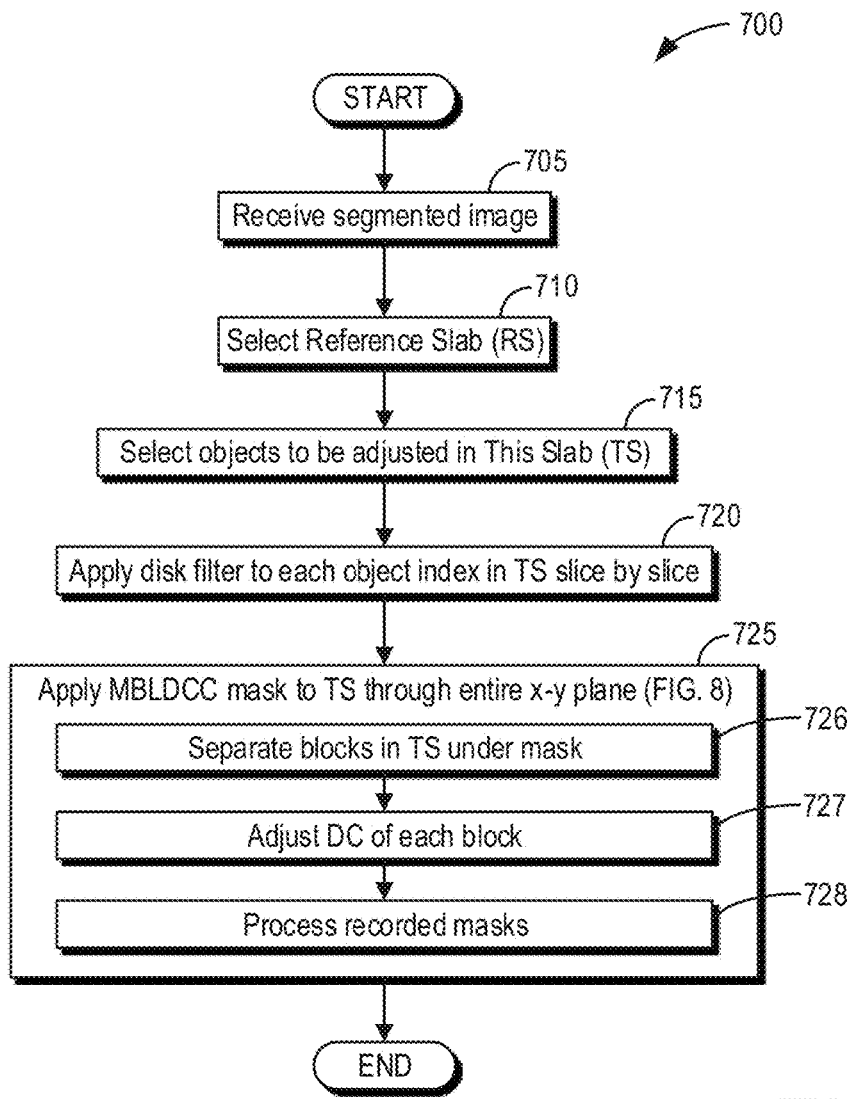
FIG. 7 shows a high-level flow chart illustrating an example method for mask-based local DC correction according to an embodiment of the invention.
Figure 8:
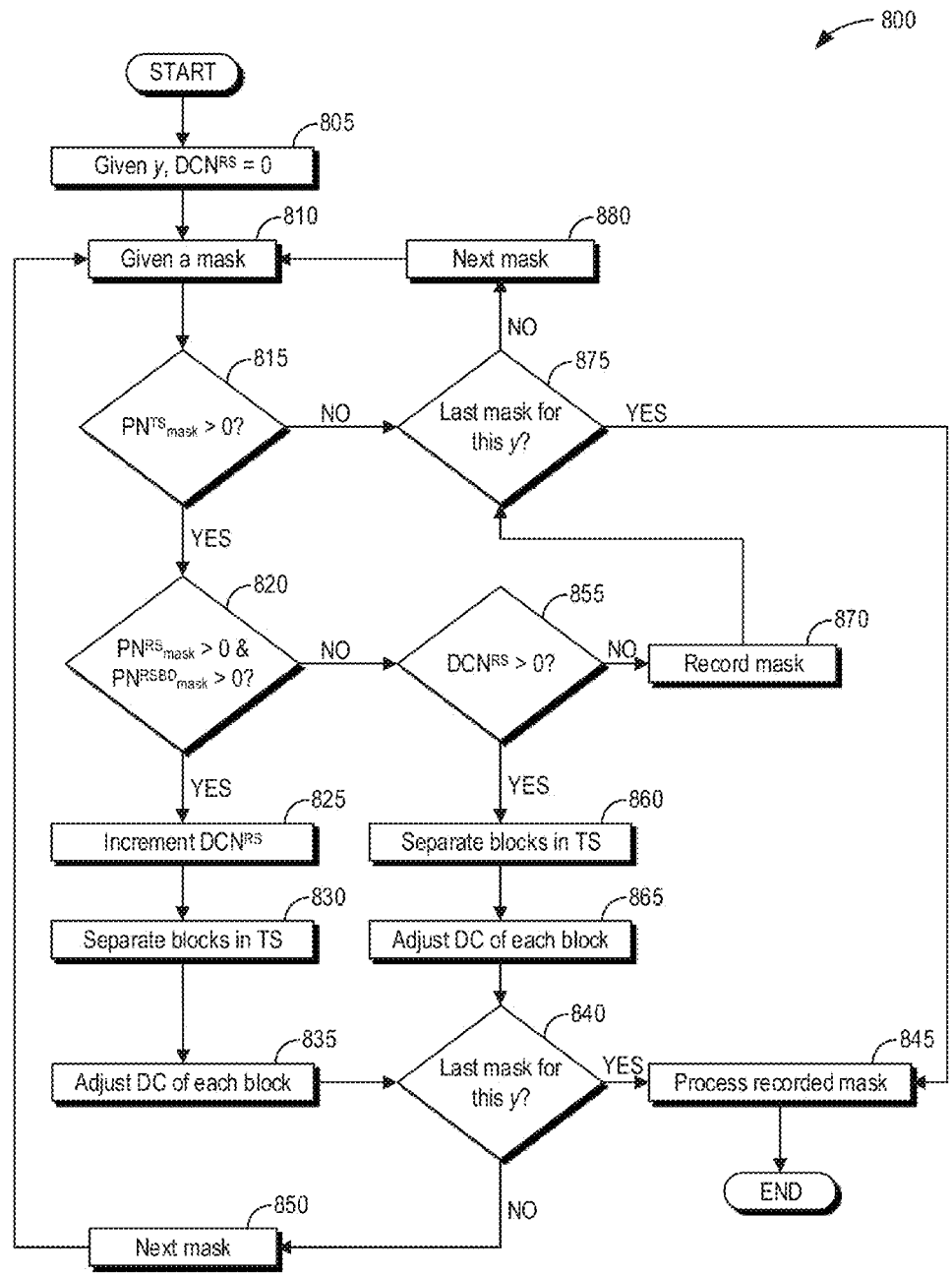
FIG. 8 shows a high-level flow chart illustrating an example method for applying a mask along a given slice according to an embodiment of the invention.
Figure 9:
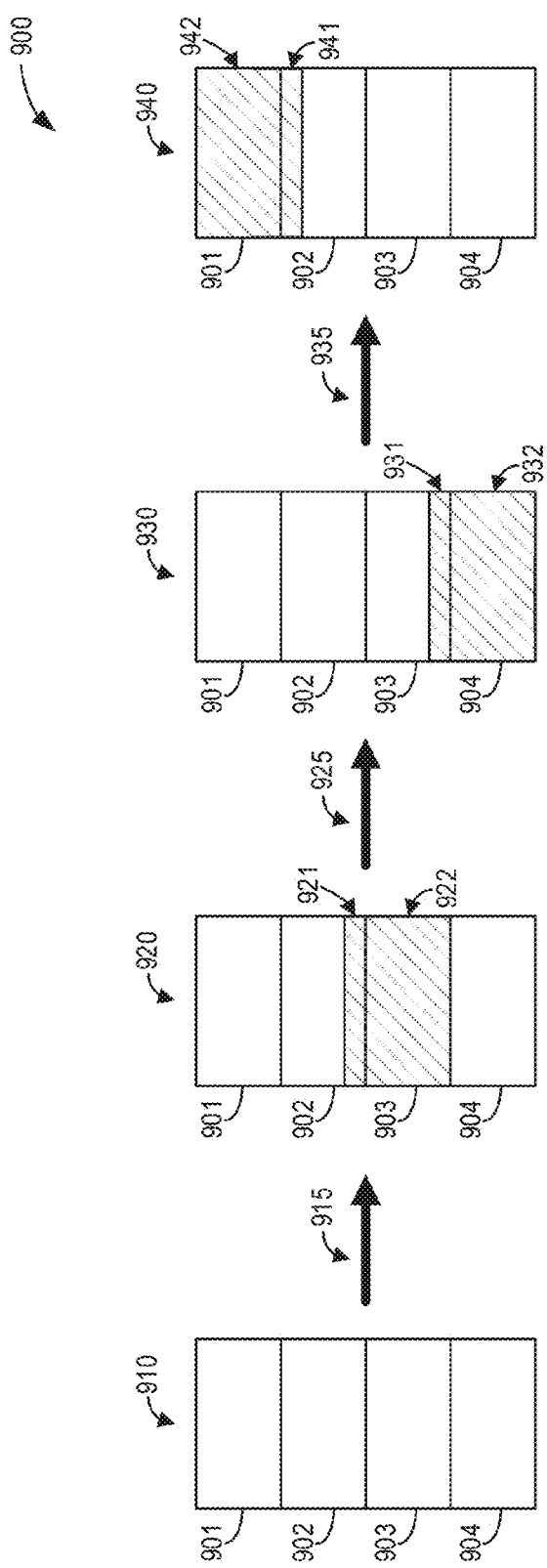
FIG. 9 shows a pictorial overview of mask-based local DC correction according to an embodiment of the invention.
Figure 10:
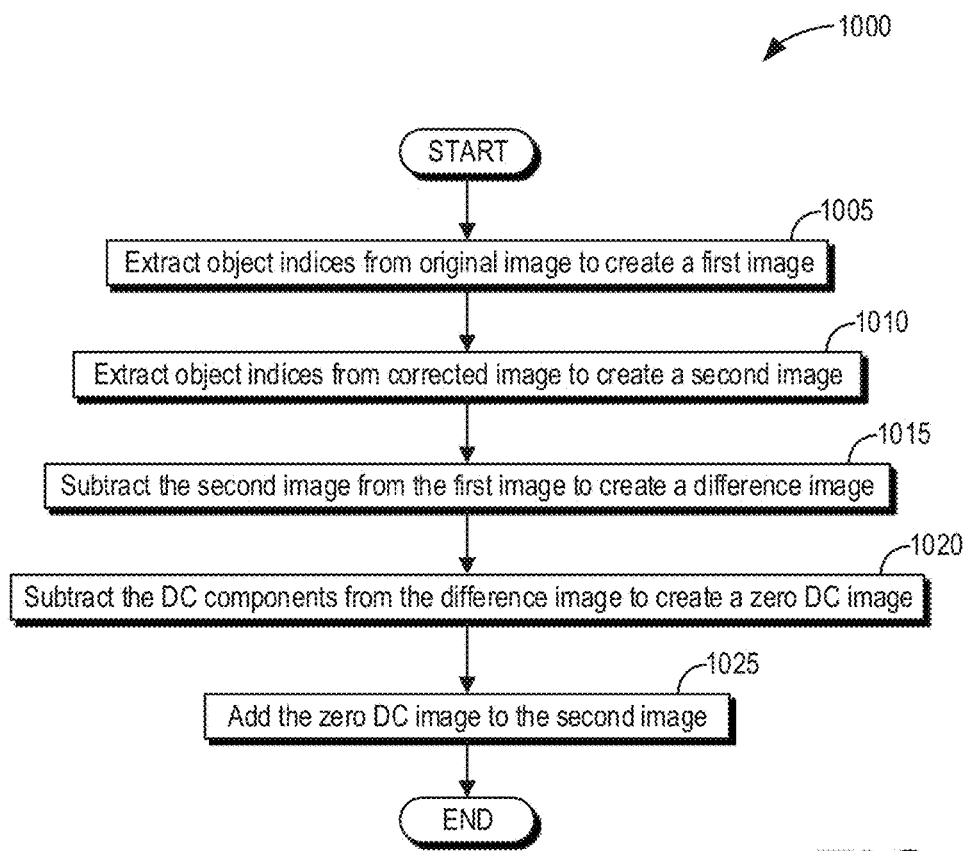
FIG. 10 shows a high-level flow chart illustrating an example method for low-frequency streak correction according to an embodiment of the invention.
Figure 11:
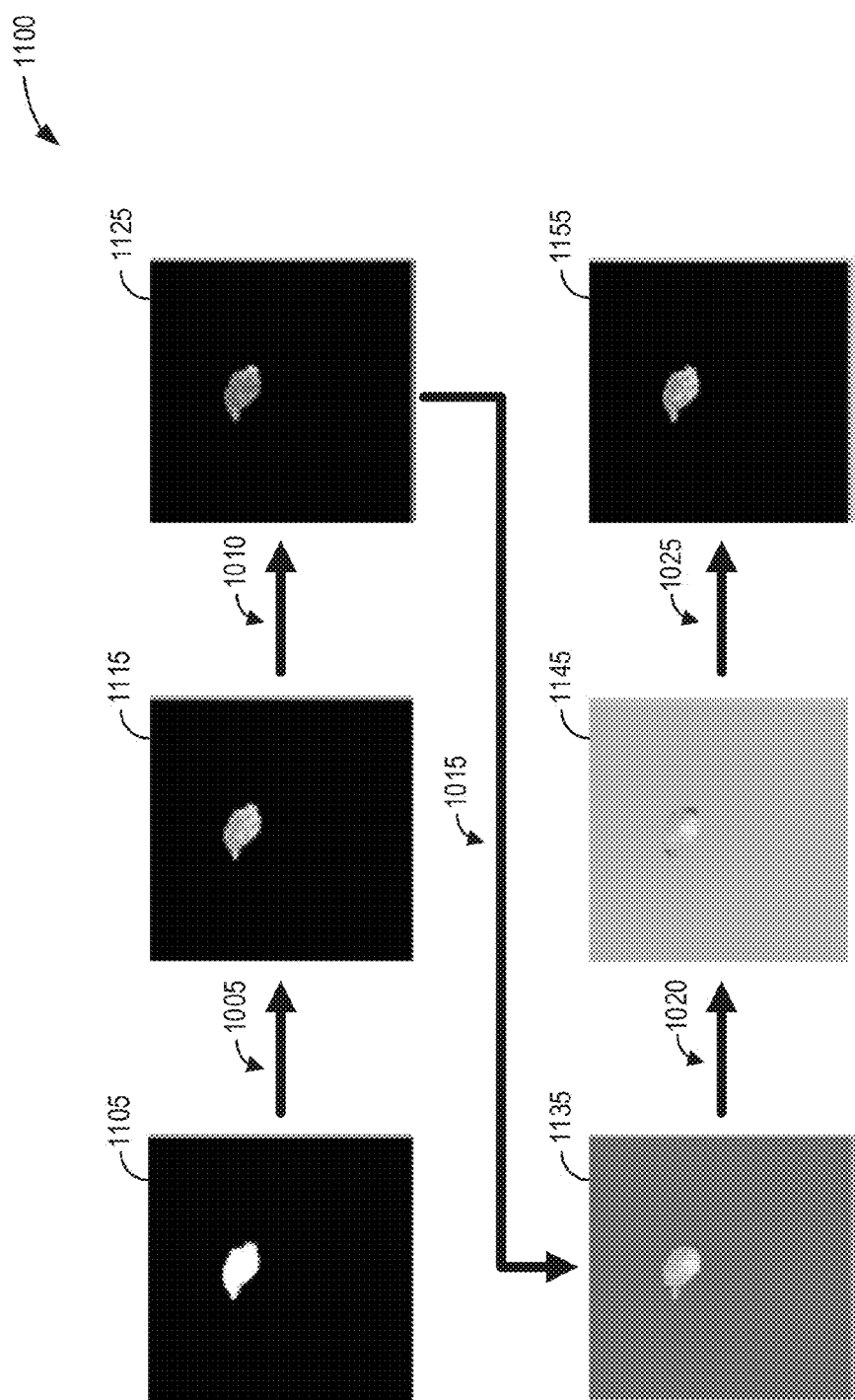
FIG. 11 shows a pictorial overview of low-frequency streak correction according to an embodiment of the invention.

The CT system depicted in FIGS. 1 and 2 may be configured to reconstruct images using data from multiple acquisitions. Each acquisition may capture a different level of contrast within the imaged subject, thereby producing contrast banding artifacts in the reconstructed image. A post-processing method for removing contrast banding artifacts includes roughly segmenting an image volume, moving a small mask throughout the image volume and adjusting DC values of the image volume, and performing streak correction, as shown in FIGS. 3 and 4. Simple segmentation may be used to isolate objects of interest in the image volume, as shown in FIGS. 5 and 6. As shown in FIGS. 7, 8, and 9, a mask-based local DC correction (MBLDCC) algorithm may normalize the DC values across multiple acquisitions, which may be interchangeably referred to hereinafter as subvolumes or slabs. Due to the motion of the mask in the MBLDCC method, low-frequency streak artifacts may be introduced to the normalized image volume. A method for performing streak correction includes adding the low frequency components incidentally removed during MBLDCC to the normalized image volume, as depicted in FIGS. 10 and 11. While cardiac imaging with a CT imaging system is utilized as a non-limiting illustrative example throughout the present disclosure, a person of ordinary skill in the art having the benefit of this disclosure will readily appreciate that the novel features of the present technology can be extended to a wide variety of imaging systems and applied to a wide variety of subjects.

FIG. 1 illustrates an exemplary CT system 100 configured to allow fast and iterative image reconstruction. Particularly, the CT system 100 is configured to image a subject such as a patient, an inanimate object, one or more manufactured parts, and/or foreign objects such as dental implants, stents, and/or contrast agents present within the body. In one embodiment, the CT system 100 includes a gantry 102, which in turn, may further include at least one X-ray radiation source 104 configured to project a beam of X-ray radiation 106 for use in imaging the patient. Specifically, the radiation source 104 is configured to project the X-rays 106 towards a detector array 108 positioned on the opposite side of the gantry 102. Although FIG. 1 depicts only a single radiation source 104, in certain embodiments, multiple radiation sources may be employed to project a plurality of X-rays 106 for acquiring projection data corresponding to the patient at different energy levels.

In certain embodiments, the CT system 100 further includes an image processing unit 110 configured to reconstruct images of a target volume of the patient using an iterative or analytic image reconstruction method. For example, the image processing unit 110 may use an analytic image reconstruction approach such as filtered backprojection (FBP) to reconstruct images of a target volume of the patient. As another example, the image processing unit 110 may use an iterative image reconstruction approach such as conjugate gradient (CG), maximum likelihood expectation maximization (MLEM), or model-based iterative reconstruction (MBIR) to reconstruct images of a target volume of the patient.

In some embodiments, a reconstructed image may include data from multiple acquisitions, sometimes referred to herein as slabs or subvolumes, taken at disjoint times. In examples where the CT system 100 is configured to image a contrast agent within a subject, each slab may include different levels of contrast as the contrast agent perfuses over time, but the same underlying anatomy. In such examples, the CT system 100 may normalize the contrast across all acquisitions, or slabs. For example, as described further herein, the CT system 100 may perform contrast correction by adjusting the DC components of one or more slabs with respect to a reference slab.

FIG. 2 illustrates an exemplary imaging system 200 similar to the CT system 100 of FIG. 1. In accordance with aspects of the present disclosure, the system 200 is configured to normalize contrast levels across multiple acquisitions in a reconstructed image volume. In one embodiment, the system 200 includes the detector array 108 (see FIG. 1). The detector array 108 further includes a plurality of detector elements 202 that together sense the X-ray beams 106 (see FIG. 1) that pass through a subject 204 such as a patient to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

In one embodiment, the system 200 includes a control mechanism 208 to control movement of the components such as rotation of the gantry 102 and the operation of the X-ray radiation source 104. In certain embodiments, the control mechanism 208 further includes an X-ray controller 210 configured to provide power and timing signals to the radiation source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The data sampled and digitized by the DAS 214 is transmitted to a computing device 216. In one example, the computing device 216 stores the data in a storage device 218. The storage device 218, for example, may include a hard disk drive, a floppy disk drive, a compact disk-read/write (CD-R/W) drive, a Digital Versatile Disc (DVD) drive, a flash drive, and/or a solid-state storage device.

Additionally, the computing device 216 provides commands and parameters to one or more of the DAS 214, the X-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates only one operator console 220, more than one operator console may be coupled to the system 200, for example, for inputting or outputting system parameters, requesting examinations, and/or viewing images. Further, in certain embodiments, the system 200 may be coupled to multiple displays, printers, workstations, and/or similar devices located either locally or remotely, for example, within an institution or hospital, or in an entirely different location via one or more configurable wired and/or wireless networks 222 such as the Internet and/or virtual private networks.

In one embodiment, for example, the system 200 either includes, or is coupled to a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a motorized table 228. Particularly, the table motor controller 226 moves the table 228 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized X-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the system 200 and instead the computing device 216 may perform one or more functions of the image reconstructor 230. Moreover, the image reconstructor 230 may be located locally or remotely, and may be operatively connected to the system 100 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 transmits the reconstructed images to the computing device 216 for generating useful patient information for diagnosis and evaluation. In certain embodiments, the computing device 216 transmits the reconstructed images and/or the patient information to a display 232 communicatively coupled to the computing device 216 and/or the image reconstructor 230.

The system 200 may enable post-processing methods for correcting contrast levels across a reconstructed image. For example, image reconstructor 230 may reconstruct images from a plurality of data acquisitions taken at disjoint times. As a result, the contrast levels may differ from slab to slab due to the perfusion of contrast during data acquisition. A method for normalizing contrast levels across slabs in a reconstructed image is described further herein and with regard to FIG. 3.

The various methods and processes described further herein may be stored as executable instructions in non-transitory memory on a computing device in system 200. In one embodiment, image reconstructor 230 may include such instructions in non-transitory memory, and may apply the methods after reconstructing an image from scanning data. In another embodiment, computing device 216 may include the instructions in non-transitory memory, and may apply the methods to a reconstructed image after receiving the reconstructed image from image reconstructor 230. In yet another embodiment, the methods and processes described herein may be distributed across image reconstructor 230 and computing device 216. For example, image reconstructor 230 may apply rough segmentation to a reconstructed image prior to transmitting the reconstructed image to computing device 216, and the computing device 216 may apply a mask-based local DC correction to the segmented image.

In one embodiment, the display 232 allows the operator to evaluate the imaged anatomy. The display 232 may also allow the operator to select a volume of interest (VOI) and/or request patient information, for example, via graphical user interface (GUI) for a subsequent scan or processing.

FIG. 3 shows a high-level flow chart illustrating an example method 300 for multi-slab contrast agent DC correction according to an embodiment of the invention. In particular, method 300 comprises a post-processing method for normalizing contrast levels across different acquisitions, or slabs, to improve image quality after image reconstruction. Method 300 may be carried out by computing device 216 and stored as executable instructions in non-transitory memory of storage device 218.

In general, method 300 is designed to only adjust the DC difference between slabs given one slab treated as a reference, so that the method will neither change high frequency components that provide important details for diagnosis nor change the imaged anatomical structures, such as the coronary arteries in a cardiac anatomy. While cardiac imaging is utilized as a non-limiting illustrative example throughout the present disclosure, method 300 may also be utilized for contrast agent corrections for other organ anatomical imaging, such as lung imaging. Furthermore, while organ anatomical imaging is utilized as a non-limiting illustrative example throughout the present disclosure, a person of ordinary skill in the art having the benefit of this disclosure will readily appreciate that method 300 may also be utilized for contrast corrections by any other imaging system configured to image any structure or structures in general.

Method 300 may begin at 305. At 305, method 300 may include generating an image. Generating an image may comprise reconstructing an image from one or more acquired datasets using system 200. Reconstructing an image may comprise applying an iterative or analytic image reconstruction method as described herein above and known in the art. The image may be reconstructed from a plurality of data acquisitions performed at different times, and thus may comprise different slabs, each with a different contrast level due to the perfusion of contrast over time.

At 310, method 300 may include applying rough segmentation to the image. The method may not depend heavily on segmentation performance, as segmentation of the cardiac chamber is a difficult task and a method that relies on segmentation may make erroneous corrections. Rough segmentation of heart chambers (i.e., the iodinated contrast agent) may be performed after subtracting a gradient image from the original image in order to better separate different chambers. The purpose of this step is to roughly segment chambers with contrast agent by selecting two thresholds (low and high) where the low threshold excludes air, fat, soft tissue, etc. and the high threshold excludes metal materials. After segmentation, different connected components in the 3D volume may be labeled. A method for rough segmentation is described further herein and with regard to FIG. 5.

At 315, method 300 may include applying a mask-based local DC correction (MBLDCC) to the segmented image.

The MBLDCC algorithm may be applied to each of the connected components. In this step, select a small cuboid mask across the whole volume and move through the x-y plane. The DC components of regions contained in the mask will be adjusted based on the DC components of regions contained in the mask in the reference slab. This method circumvents the difficulty of direct segmentation, of each agent region in the volume by using local summations rather than compensating for the entire connected component at once. A method for MBLDCC is described further herein and with regard to FIG. 7.

At 320, method 300 may include applying a low-frequency streaks correction to the contrast-corrected image. The MBLDCC algorithm may roughly adjust the DC components of a slab to an acceptable level. However, there may be some low frequency streak artifacts introduced by the moving directions of the mask. In order to overcome this difficulty, the result is improved with a zero DC component difference image, which is the difference between the original image and the adjusted image (i.e. the image with the correct DC but streak artifacts possible). A method for low-frequency streak correction is described further herein and with regard to FIG. 10.

At 325, method 300 may include outputting the image. Method 300 may then end.

FIG. 4 shows a pictorial overview 400 of multi-slab contrast agent DC correction according to an embodiment of the invention. In particular, overview 400 illustrates method 300 described hereinabove with regard to FIG. 3.

Original image 405 comprises a plurality of subvolumes formed during image reconstruction from a plurality of datasets acquired at disjoint times. As a result of the disjoint times, original image 405 may include contrast banding artifacts due to differing levels of contrast agent from subvolume to subvolume.

Process 410 may remove the contrast banding artifacts by normalizing the zero-frequency components of each subvolume to match the zero-frequency component of a reference subvolume. As described hereinabove, process 410 may thus include applying rough segmentation and MBLDCC to the original image 410 to generate a contrast-normalized image 415.

Process 410 may introduce streak artifacts to the image due to the directional movement of the mask, as seen in contrast-normalized image 415. Process 420 includes subtracting streaks from image to generate a final streak-corrected and contrast-normalized image 425.

FIG. 5 shows a high-level flow chart illustrating an example method 500 for applying rough segmentation according to an embodiment of the invention. In particular, method 500 relates to roughly segmenting an image to distinguish components containing contrast agent from non-contrast-enhanced components. Method 500 may be carried out by computing device 216 and stored as executable instructions in non-transitory memory of storage device 218.

At 505, method 500 may include receiving image input. Receiving image input may comprise receiving a reconstructed image. In one embodiment, receiving image input may comprise receiving a single subvolume of a reconstructed image, where the subvolume includes data from a single data acquisition, while in another embodiment, receiving image input may comprise receiving all subvolumes of a reconstructed image, where each subvolume corresponds to a different acquisition. Regardless of the number of subvolumes received at 505, the subsequent steps of method 500 may be applied to each subvolume.

At 510, method 500 may include calculating upper and lower thresholds. The upper threshold may be empirically selected to exclude materials with high Hounsfield units (HU) such as metal and very dense swirling contrast. The lower threshold may be calculated using, for example, a Gonzalez & Woods algorithm to exclude low HU materials such as soft tissue, fat, air, etc. For example, in order to calculate a threshold of an image using a Gonzalez & Woods algorithm, the computing device may initialize the threshold T with an initial threshold $T_0$ comprising the average of the maximum value and minimum value of the image. The computing device may then segment the image using the initial threshold $T_0$ to generate two groups of image pixels, one group with image pixels smaller or equal to the initial threshold $T_0$ and another group with image pixels larger than the initial threshold $T_0$. The computing device may then calculate the average pixel values of the two groups. The computing device may then calculate a new threshold $T_1$ which is the mean value of the averages of the two groups. The computing device may repeat the above steps using the new threshold $T_1$ as the initial threshold. The computing device may repeat the above steps N times until the absolute difference between the new threshold $T_{N+1}$ and the preceding threshold $T_N$ is smaller than a specified number. The computing device may then use the final threshold obtained as the lower threshold.

After calculating the upper and lower thresholds, method 500 may continue to 515. At 515, method 500 may include applying simple segmentation to the image using the calculated thresholds. Segmenting the image may comprise partitioning the image into different objects. For example, the two thresholds may be used to roughly segment the heart chambers and great vessels which are filled with contrast agent. In one example, the simple segmentation is performed based on the difference image volume between the original image volume and the gradient image volume. Segmentation produces a binary image volume with the same dimension of the input image volume.

Continuing at 520, method 500 may include applying a binary mask to the segmented image slice by slice. Based on the binary image volume, small objects which are not heart chamber regions may be removed and small holes in the mask which are mainly in the heart chamber regions may be filled slice by slice. At 525, method 500 may include deleting regions with an area smaller than a number of pixels $N_{ad}$. At 530, method 500 may include filling holes with an area smaller than a number of pixels $N_{hf}$.

At 535, method 500 may include applying labels to separated components in the final 3D binary image volume. After the separated components are labeled, the segmented imaged is ready for the application of MBLDCC. At 540, method 500 may include outputting the segmented image. Method 500 may then end.

FIG. 6 shows a pictorial overview 600 illustrating a method for rough segmentation according to an embodiment of the invention. In particular, overview 600 illustrates the steps of method 500 shown in FIG. 5.

Original image volume 605 comprises a reconstructed image without any post-reconstruction processing. Upper and lower thresholds may be determined using original image volume 605. After calculating the upper and lower thresholds as described at step 510 of FIG. 5, the thresholds are used to roughly segment the original image volume using step 515, thereby producing a roughly segmented image volume 615.

Step 620 comprises the generation of a binary mask 625 of appropriate size to cover the components of interest in the image volume. Step 520 comprises applying the binary mask 625 to the roughly segmented image volume 615 to remove components of the segmented image volume outside of area of the binary mask, as shown by the masked image volume 635.

Step 525 may be applied to the masked image volume 635 to delete regions of the masked image volume 635 with an area smaller than a number of pixels $N_{ad}$, thereby producing the image volume 645. Step 530 may then be applied to image volume 645 to delete regions of the image volume 645 with an area larger than a number of pixels $N_{hf}$, thereby producing the final image volume 655.

The final image volume 655 comprises a segmented image volume containing contrast-enhanced components. Each separate component may be labeled with an object index to identify each distinct component. Once the components are labeled, the image volume 655 is prepared for mask-based local DC correction as described herein with regard to FIG. 7.

FIG. 7 shows a high-level flow chart illustrating an example method 700 for mask-based local DC correction according to an embodiment of the invention. In particular, method 700 relates to normalizing the zero-frequency, or DC, components of each subvolume, or slab, in a reconstructed image. Method 700 may be carried out by computing device 216 and stored as executable instructions in non-transitory memory of storage device 218.

Method 700 may begin at 705. At 705, method 700 may include receiving a segmented image volume. The segmented image volume may be segmented according to the method 500 shown in FIG. 5 and described herein above. However, the segmented image volume may be segmented according to a different segmentation method without departing from the scope of the present disclosure.

At 710, method 700 may include selecting a reference slab (RS). In one example, the reference slab may be automatically selected based on a pre-determined order of the slabs. In another example, the reference slab may be automatically selected based on the contrast levels of each slab, with the selection of a particular slab as the reference slab based on the contrast level of the particular slab within a pre-specified range. In yet another example, the reference slab may be manually selected by an operator of system 200, for example, using operator console 220. The DC components of each other slab comprising the segmented image may be adjusted based on the DC component of the RS. Regarding terminology, the slab actively being corrected with respect to the RS may be referred to hereinafter as This Slab (TS).

At 715, method 700 may include selecting objects to be adjusted in This Slab (TS). As described herein with regard to FIG. 5, separate components of the image volume may be labeled. However, not all components may need to be corrected. In order to select objects to be adjusted and to exclude objects that do not need to be adjusted, the computing device may calculate the number of voxel numbers in each object for RS and TS. If the voxel numbers in both slabs are larger than zero, then the object under consideration may need to be corrected. If the voxel number of a given object either in RS or in TS is equal to zero, the computing device may not apply MBLDCC to the object because either there is no reference DC available in RS or there is no need to correct the DC component in TS.

Continuing at 720, method 700 may include applying a disk filter to each object index in TS slice by slice. For each 3D object selected for correction at step 715, a 2D disk filter of a specified radius may be applied to the object indices of the object slice by slice. Applying a disk filter in this way ensures a smooth change between the object boundaries and the background. In the absence of applying the disk filter to the object index, there may be sharp changes in the object boundaries and small hole boundaries.

At 725, method 700 may include applying an MBLDCC mask to TS through the entire x-y plane. At 726, method 700 may include separating blocks in TS under mask. At 727, method 700 may include adjusting the DC level of each block. At 728, method 700 may include processing the recorded masks. A method for applying the MBLDCC for a given value of y is described further herein and with regard to FIG. 8.

After applying the MBLDCC mask to TS, method 700 may end. Method 700 may be repeated for each slab. An example workflow for applying method 700 to each slab is described further herein and with regard to FIG. 9.

FIG. 8 shows a high-level flow chart illustrating an example method 800 for applying a mask along a given slice according to an embodiment of the invention. In particular, method 800 relates to correcting a DC level of a slab in accordance with method 700 for a given value of y. Method 800 may be carried out by computing device 216 and stored as executable instructions in non-transitory memory of storage device 218.

Method 800 may begin at 805. At 805, method 800 may include setting the counted DC component number in RS as the mask moves, or $DCN^{RS}$, equal to zero for a given value of y.

At 810, method 800 may include being given a mask. At 815, method 800 may include determining if the pixel number in TS under the current mask, or $pN^{TS}_{mask}$, is greater than zero. If $PN^{TS}_{mask}$ is greater than zero, the underlying object may be corrected by MBLDCC. However, if $PN^{TS}_{mask}$ is equal to zero, there may be no need to correct the DC component in TS as there is nothing to correct at this position of the mask.

Thus, if $PN^{TS}_{mask}$ is greater than zero, method 800 may continue to 820. At 820, method 800 may include determining if the pixel number in RS under the current mask, or $PN^{RS}_{mask}$, is greater than zero and if the pixel number in RS within slices touching the slab boundary smaller than the boundary definition under the current mask, or $PN^{RSBD}_{mask}$, is greater than zero. If $PN^{RS}_{mask}$ equals zero, there may not be a reference DC value in RS. If $PN^{RSBD}_{mask}$ is greater than zero, an object may be touching and/or crossing the slab boundary between RS and TS.

If $PN^{RS}_{mask}$ and $PN^{RSBD}_{mask}$ are both greater than zero, method 800 may proceed to 825. At 825, method 800 may include incrementing $DCN^{RS}$ by one to denote that the DC component number in RS as the mask moves has increased.

At 830, method 800 may include separating blocks in TS under the mask. If there is only one block under the mask in TS, step 830 is trivial. However, there may be two or more blocks with different DC components in TS. Adjusting the DC components of two or more blocks in TS with the same reference value may result in errors.

At 835, method 800 may include adjusting the DC level, or zero-frequency component, of each block. If there is a block touching the slab boundary, the DC component of this block may be adjusted by the DC component in the RS. If there is a block not touching the slab boundary, the DC component of this block may be adjusted based on average DC components in the RS.

At 840, method 800 may determine if the given mask is the last mask for this value of y. If so, method 800 may proceed to 845, where method 800 may include processing the recorded mask. Processing the recorded mask may comprise adjusting any blocks that were not adjusted, for example, because an average DC component value in RS was not available to adjust the block. Method 800 may then end.

Returning to 840, if the given mask is not the last mask for this value of y, method 800 may proceed to 850 where the next mask is assigned. Method 800 may then return to step 810 as shown.

Returning to 820, if $PN^{RS}_{mask}$ and $PN^{RSBD}_{mask}$ are not both greater than zero, then there may not be RS DC component value available for adjusting blocks in TS, and method 800 may continue to 855. At 855, method 800 may include determining if $DCN^{RS}$ is greater than zero. If $DCN^{RS}$ is greater than zero, then an average DC component value for RS is available for adjusting blocks in TS, and method 800 may continue to 860, where method 800 may include separating blocks in TS. At 865, method 800 may include adjusting the DC component of each block. Adjusting the DC component of each block may comprise adjusting the DC component of a block in TS using the average DC component from the RS. Method 800 may then continue to step 840 and proceed as described hereinabove.

Returning to 855, if $DCN^{RS}$ is not greater than zero, then method 800 may include recording the mask at 870. Recording the mask comprises saving the mask for later processing, for example at 845 an average DC component value may be used to adjust the DC component of the blocks under the saved mask.

Method 800 may then continue to 875 to determine if the given mask is the last mask for this value of y. If the given mask is the last mask for this value of y at 875, method 800 may proceed to 845, where the method may include processing the recorded mask before ending. If the given mask is not the last mask for this value of y, method 800 may continue to 880, where the next mask is assigned.

Returning to 815, if $PN^{TS}_{mask}$ is not greater than zero, then there are no blocks that need to be adjusted under the mask. Method 800 may continue to 875 and proceed as described hereinabove.

FIG. 9 shows a pictorial overview 900 illustrating a mask-based local DC correction according to an embodiment of the invention. In particular, overview 900 illustrates how the methods of FIGS. 7 and 8 may be sequentially applied to multiple slabs. Overview 900 depicts an image volume 910 comprising four subvolumes, or slabs, shown in FIG. 9 as first slab 901, second slab 902, third slab 903, and fourth slab 904. However, in other examples, an image volume may comprise more than four slabs or less than four slabs.

At step 915, a reference slab (RS) is selected from the four slabs. In particular, the second slab 902 is selected as the RS. The shaded portion of image volume 920 depicts where the MBLDCC methods described herein with regard to FIGS. 7 and 8 may be applied. The shaded portion 921 of second slab 902 functions as the RS, while the shaded portion 922 of the third slab 903 functions as This Slab (TS). RS 921 is located directly adjacent to TS 922 in order to provide continuity in DC values at the slab boundary.

After mask-based local DC corrections are applied to TS 922, step 925 selects the third slab 903 as the RS and the fourth slab 904 as TS for the image volume 930, where image volume 930 includes the DC corrections to the third slab 903. In particular, the shaded portion 931 of the third slab 903 is the RS and the shaded portion 932 of the fourth slab 904 is TS. The MBLDCC is applied to TS 932 using RS 931 until all DC values are corrected for the fourth slab 904.

After MBLDCC is applied to the fourth slab 904, step 935 selects the second slab 902 as the RS and the first slab 901 as TS for the image volume 940, where image volume 940 includes the DC corrections to the third slab 903 and the fourth slab 904. In particular, the shaded portion 941 of the second slab 902 functions as the RS and the shaded portion 942 of the first slab 901 functions as TS, where RS 941 is directly adjacent to TS 942. Using DC component values of RS 941 to adjust DC component values of TS 942 ensures continuity of DC component values across the slab boundary between first slab 901 and second slab 902.

After applying the MBLDCC to normalize the contrast across slabs, the corrected images may have an improved quality in the sagittal view. However, the axial images may contain streak artifacts caused by the moving direction of the mask. Changing the moving direction of the mask may correct such artifacts in the axial images. However, correcting the streak artifacts in the axial images in such a manner may introduce similar streak artifacts in the coronal images. As described further herein with regard to FIGS. 10 and 11, a low-frequency streak correction may ensure that only the DC components were removed and thereby remove all streak artifacts caused by the moving mask of the MBLDCC method.

FIG. 10 shows a high-level flow chart illustrating an example method 1000 for low-frequency streak correction according to an embodiment of the invention. In particular, method 1000 relates to the removal of low-frequency streak artifacts from images corrected using MBLDCC. Method 1000 may carried out by computing device 216 and stored as executable instructions in non-transitory memory of storage device 218.

Method 1000 may begin at 1005. At 1005, method 1000 may include extracting object indices from the original image to create a first image. Object indices may comprise the segmented and labeled objects obtained using method 500, for example. As a result, the first image may comprise a portion of the original, uncorrected image corresponding to the one or more labeled objects.

At 1010, method 1000 may include extracting object indices from the corrected image to create a second image. Similar to the first image, the second image may comprise a portion of the corrected image corresponding to the one or more labeled objects.

Continuing at 1015, method 1000 may include subtracting the second image from the first image to create a difference image. The difference image may comprise the differences between the original and the corrected images.

At 1020, method 1000 may include subtracting the DC components from the difference image to create a zero DC image. By subtracting the DC components from the difference image, the zero DC image comprises the low-frequency differences between the first and second images while excluding the DC component corrections.

At 1025, method 1000 may include adding the zero DC image to the second image to produce a final image. By adding the zero DC image to the second image, the low-frequency components incidentally removed during MBLDCC may be added back to the corrected image. The final image thus comprises a DC-corrected image that leaves non-zero frequency components of the image untouched, thereby preserving anatomic structure. Method 1000 may then end.

FIG. 11 shows a pictorial overview 1100 illustrating low-frequency streak correction according to an embodiment of the invention. In particular, overview 1100 illustrates the method 1000 described herein above with regard to FIG. 10.

Object indices image 1105 comprises the isolated object indices. Step 1005 as described herein with regard to FIG. 10 is applied to the original image. For example, the object indices image 1105 may be applied to the original image as a mask to remove all image data except for the objects. As shown by image 1115, the object indices are extracted from the original image to isolate the object indices of the original image.

Step 1010 is applied to the corrected image. For example, the object indices image 1105 may be applied to the corrected image as a mask to remove all image data except for the objects. As shown by image 1125, the object indices are extracted from the corrected image to isolate the object indices of the corrected image.

Step 1015 is applied to image 1115 and image 1125. In particular, the corrected image 1125 is subtracted from the original image 1115 to produce the difference image 1135.

Step 1020 is then applied to the difference image 1135. As shown, the zero-frequency components are subtracted from the difference image to produce the zero-frequency difference image 1145. The zero-frequency difference image 1145 includes the image components that were incidentally removed from the original image by the MBLDCC.

Step 1025 is then applied to the zero-frequency difference image 1145. In particular, the zero-frequency difference image 1145 is added to the corrected image 1125 to produce the streak-corrected image 1155. The streak-corrected image 1155 includes the DC corrections shown in image 1125 in addition to the low-frequency image data shown in the zero-frequency difference image 1145. In this way, streak artifacts may be eliminated from the final corrected image without further adjusting the DC components.

The technical effect of the disclosure may include the creation of a reconstructed image with normalized contrast levels across multiple acquisitions. Another technical effect of the disclosure may include the removal of streak artifacts from a normalized image.

In one embodiment, a method for computed tomography imaging comprises generating an original image comprising multiple subvolumes, segmenting the original image into different structures of an organ for each subvolume, selectively applying a mask-based correction through each area of a subvolume that includes structures of an organ to generate an updated image, and performing streak correction between the original image and the updated image to generate a final image. The method further comprises selecting an upper threshold and a lower threshold based on the original image. Segmenting the original image comprises applying simple segmentation based on the upper threshold and the lower threshold.

In one example, segmenting the original image further comprises deleting regions of the original image with an area smaller than a first number of pixels. In another example, segmenting the original image further comprises filling holes of the original image with an area smaller than a second number of pixels. In yet another example, segmenting the original image further comprises labeling the different structures of the organ.

In one example, selectively applying a mask-based correction comprises applying a three-dimensional mask to a portion of a reference subvolume and a portion of a selected subvolume, and adjusting a first value of the selected subvolume within the mask based on a second value of the reference subvolume within the mask. For example, the first value and the second value comprise a zero-frequency component of the image.

The method further comprises selecting an object in the portion of the selected subvolume. Adjusting the first value based on the second value is based on a distance of the object from the reference subvolume.

In one example, the reference subvolume is automatically pre-selected. In another example, the reference subvolume is manually selected by an operator.

In one example, performing streak correction comprises subtracting the updated image from the original image to generate a difference image, subtracting zero-frequency components from the difference image to generate a low-frequency image, and adding the low-frequency image to the updated image.

In another embodiment, a workflow method for medical imaging procedures comprises: receiving image data from an imaging device to a computer, wherein the image data includes subvolumes corresponding to different image acquisition times; determining whether the image data includes contrast banding artifacts based on contrast levels of the subvolumes; applying an image correction algorithm to normalize the contrast levels across the subvolumes; and displaying corrected image data. In one example, applying the image correction algorithm comprises adjusting one or more zero-frequency components of the image data.

In yet another embodiment, a system comprises: a data storage device storing one or more routines; and a computing device configured to execute the one or more routines stored in the data storage device, wherein the one or more routines, when executed by the computing device, cause the computing device to: generate an original image comprising multiple subvolumes; segment the original image into different structures for each subvolume; selectively apply a mask-based correction through each area of a subvolume that includes continuous structures to generate an updated image; and perform streak correction between the original image and the updated image to generate a final image. The one or more routines, when executed by the computing device, further cause the computing device to calculate an upper threshold and a lower threshold based on the original image, and wherein segmenting the image into the different structures is based on the upper and the lower thresholds.

In one example, selectively applying a mask-based correction comprises applying a three-dimensional mask to a portion of a reference subvolume and a portion of a selected subvolume, and adjusting a first value of the selected subvolume within the mask based on a second value of the reference subvolume within the mask. For example, the first value and the second value comprise a zero-frequency component of the image.

In another example, the computer is further programmed to select an object in the portion of the selected subvolume. In such an example, adjusting the first value based on the second value is based on a distance of the object from the reference subvolume. In one example, the reference subvolume is automatically preselected.

In yet another example, performing streak correction comprises subtracting the updated image from the original image to generate a difference image, subtracting zero-frequency components from the difference image to generate a low-frequency image, and adding the low-frequency image to the updated image.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for imaging, comprising:
   generating an original image comprising multiple subvolumes;
   segmenting the original image into different structures for each subvolume;
   selectively applying a mask-based correction through each area of a subvolume that includes continuous structures to generate an updated image; and
   performing streak correction between the original image and the updated image to generate a final image.

2. The method of claim 1, further comprising selecting an upper threshold and a lower threshold based on the original image, and wherein segmenting the original image comprises applying simple segmentation based on the upper threshold and the lower threshold.

3. The method of claim 2, wherein segmenting the original image further comprises deleting regions of the original image with an area smaller than a first number of pixels.

4. The method of claim 2, wherein segmenting the original image further comprises filling holes of the original image with an area smaller than a second number of pixels.

5. The method of claim 1, wherein segmenting the original image further comprises labeling the different structures.

6. The method of claim 1, wherein selectively applying a mask-based correction comprises applying a three-dimensional mask to a portion of a reference subvolume and a portion of a selected subvolume, and adjusting a first value of the selected subvolume within the mask based on a second value of the reference subvolume within the mask.

7. The method of claim 6, wherein the first value and the second value comprise a zero-frequency component of the image.

8. The method of claim 6, further comprising selecting an object in the portion of the selected subvolume, and wherein adjusting the first value based on the second value is based on a distance of the object from the reference subvolume.

9. The method of claim 6, wherein the reference subvolume is automatically preselected.

10. The method of claim 6, wherein the reference subvolume is manually selected by an operator.

11. The method of claim 1, wherein performing streak correction comprises subtracting the updated image from the original image to generate a difference image, subtracting zero-frequency components from the difference image to generate a low-frequency image, and adding the low-frequency image to the updated image.

12. A workflow method for medical imaging procedures, comprising:
    receiving image data from an imaging device to a computer, wherein the image data includes subvolumes corresponding to different image acquisition times;
    determining whether the image data includes contrast banding artifacts based on contrast levels of the subvolumes;
    applying an image correction algorithm to normalize the contrast levels across the subvolumes; and
    displaying corrected image data.

13. The workflow method of claim 12, wherein the applying the image correction algorithm comprises adjusting one or more zero-frequency components of the image data.

14. A system, comprising:
    a data storage device storing one or more routines; and
    a computing device configured to execute the one or more routines stored in the data storage device, wherein the one or more routines, when executed by the computing device, cause the computing device to:
        generate an original image comprising multiple subvolumes;
        segment the original image into different structures for each subvolume;
        selectively apply a mask-based correction through each area of a subvolume that includes continuous structures to generate an updated image; and
        perform streak correction between the original image and the updated image to generate a final image.

15. The system of claim 14, wherein the one or more routines, when executed by the computing device, further cause the computing device to calculate an upper threshold and a lower threshold based on the original image, and wherein segmenting the image into the different structures is based on the upper and the lower thresholds.

16. The system of claim 14, wherein selectively applying a mask-based correction comprises applying a three-dimensional mask to a portion of a reference subvolume and a portion of a selected subvolume, and adjusting a first value of the selected subvolume within the mask based on a second value of the reference subvolume within the mask.

17. The system of claim 16, wherein the first value and the second value comprise a zero-frequency component of the image.

18. The system of claim 16, wherein the one or more routines, when executed by the computing device, further cause the computing device to select an object in the portion of the selected subvolume, and wherein adjusting the first value based on the second value is based on a distance of the object from the reference subvolume.

19. The system of claim 16, wherein the reference subvolume is automatically preselected.

20. The system of claim 14, wherein performing streak correction comprises subtracting the updated image from the original image to generate a difference image, subtracting zero-frequency components from the difference image to generate a low-frequency image, and adding the low-frequency image to the updated image.

* * * * *